(12) United States Patent
Donehoo et al.

(10) Patent No.: US 8,211,030 B2
(45) Date of Patent: Jul. 3, 2012

(54) NIBP TARGET INFLATION PRESSURE AUTOMATION USING DERIVED SPO$_2$ SIGNALS

(75) Inventors: Robert F. Donehoo, Colgate, WI (US); Lawrence T. Hersh, Milwaukee, WI (US); Sai Kolluri, Mequon, WI (US)

(73) Assignee: The General Electric Company, Schenectady, NY (US)

(*) Notice: Subject to any disclaimer, the term of this patent is extended or adjusted under 35 U.S.C. 154(b) by 448 days.

(21) Appl. No.: 12/412,057

(22) Filed: Mar. 26, 2009

(65) Prior Publication Data

US 2010/0249616 A1    Sep. 30, 2010

(51) Int. Cl.
*A61B 5/02* (2006.01)
(52) U.S. Cl. ......................... 600/494; 600/485
(58) Field of Classification Search .......... 600/302–308, 600/345–371, 481–507, 529–545; 606/201–202
See application file for complete search history.

(56) References Cited

U.S. PATENT DOCUMENTS

| | | |
|---|---|---|
| 4,360,029 A | 11/1982 | Ramsey, III |
| 4,394,034 A | 7/1983 | Murphy et al. |
| 4,461,226 A | 7/1984 | Tajima |
| 4,543,962 A | 10/1985 | Medero et al. |
| 4,546,775 A | 10/1985 | Medero |
| 4,638,810 A | 1/1987 | Ramsey, III et al. |
| 4,754,761 A | 7/1988 | Ramsey, III et al. |
| 4,776,339 A | 10/1988 | Schreiber |
| 4,780,824 A | 10/1988 | Niwa et al. |
| 4,796,184 A | 1/1989 | Bahr et al. |
| 4,889,133 A | 12/1989 | Nelson et al. |
| 4,928,701 A | 5/1990 | Harada et al. |
| 4,949,710 A | 8/1990 | Dorsett et al. |
| 5,052,397 A | 10/1991 | Ramsey, III et al. |
| 5,170,795 A | 12/1992 | Ramsey, III et al. |
| 5,261,414 A | 11/1993 | Aung et al. |
| 5,267,567 A | 12/1993 | Aung et al. |
| 5,279,303 A | 1/1994 | Kawamura et al. |
| 5,309,908 A | 5/1994 | Friedman et al. |
| 5,577,508 A | 11/1996 | Medero |

(Continued)

OTHER PUBLICATIONS

Takazawa K, Tanaka H, Fujita M, et al. Assessment of vasoactive agents and vascular aging by the second derivative of photoplethysmogram waveform Hypertension 1998;32:365-370.*

*Primary Examiner* — Navin Natnithithadha
*Assistant Examiner* — Sunita Reddy
(74) *Attorney, Agent, or Firm* — Andrus, Sceales, Starke & Sawall, LLP (57) ABSTRACT

A method and system for operating a non-invasive blood pressure monitor that utilizes an SpO$_2$ plethysmograph waveform to determine the initial inflation pressure for the NIBP monitor. A pulse sensor is placed on the patient's limb distal to the blood pressure cuff and provides a pulse waveform to the NIBP monitor. The NIBP monitor calculates a second derivative of the pulse waveform, which includes a series of acceleration peaks corresponding to pulse signals within the pulse waveform. When the blood pressure cuff reaches systolic pressure, the acceleration peaks contained within the acceleration waveform are eliminated, thus providing an indication that the cuff pressure has reached systolic pressure for the patient. Use of the SPO$_2$ plethysmograph signal to determine the initial inflation pressure reduces both the over-inflation of the blood pressure cuff and the under-inflation of the blood pressure cuff, which increases the rate at which the blood pressure measurement can be made while increasing patient comfort.

17 Claims, 6 Drawing Sheets

U.S. PATENT DOCUMENTS

| | | | | |
|---|---|---|---|---|
| 5,579,776 | A | 12/1996 | Medero | |
| 5,590,662 | A | 1/1997 | Hersh et al. | |
| 5,704,362 | A | 1/1998 | Hersh et al. | |
| 5,730,139 | A | 3/1998 | Miyazaki et al. | |
| 5,743,857 | A | 4/1998 | Shinoda et al. | |
| 5,830,149 | A | 11/1998 | Oka et al. | |
| 5,836,887 | A | 11/1998 | Oka et al. | |
| 5,865,756 | A | 2/1999 | Peel, III | |
| 5,921,936 | A | 7/1999 | Inukai et al. | |
| 6,007,492 | A | 12/1999 | Goto et al. | |
| 6,027,455 | A | 2/2000 | Inukai et al. | |
| 6,036,651 | A | 3/2000 | Inukai et al. | |
| 6,241,680 | B1 | 6/2001 | Miwa | |
| 6,251,081 | B1 | 6/2001 | Narimatsu | |
| 6,358,213 | B1 | 3/2002 | Friedman et al. | |
| 6,423,010 | B1 | 7/2002 | Friedman et al. | |
| 6,440,080 | B1 | 8/2002 | Booth et al. | |
| 6,491,638 | B2 | 12/2002 | Oka | |
| 6,589,183 | B2 | 7/2003 | Yokozeki | |
| 6,602,198 | B2 | 8/2003 | Yokozeki | |
| 6,645,154 | B2 | 11/2003 | Oka | |
| 6,648,828 | B2 | 11/2003 | Friedman et al. | |
| 7,300,404 | B1 | 11/2007 | Kolluri et al. | |
| 7,390,302 | B2 | 6/2008 | Friedman et al. | |
| 7,462,152 | B2 | 12/2008 | Kolluri et al. | |
| 2002/0052552 | A1 | 5/2002 | Yokozeki | |
| 2002/0082507 | A1 | 6/2002 | Kolluri et al. | |
| 2003/0135087 | A1* | 7/2003 | Hickle et al. | 600/26 |
| 2003/0167012 | A1 | 9/2003 | Friedman et al. | |
| 2004/0171943 | A1* | 9/2004 | Hersh et al. | 600/490 |
| 2004/0186386 | A1* | 9/2004 | Kolluri et al. | 600/500 |
| 2005/0004477 | A1* | 1/2005 | Friedman et al. | 600/485 |
| 2006/0229519 | A1* | 10/2006 | Fujiwara et al. | 600/500 |
| 2007/0016085 | A1* | 1/2007 | Inukai et al. | 600/485 |
| 2007/0106163 | A1 | 5/2007 | Friedman et al. | |
| 2007/0118036 | A1* | 5/2007 | Hersh et al. | 600/485 |
| 2007/0123784 | A1* | 5/2007 | Hersh et al. | 600/490 |
| 2007/0208240 | A1* | 9/2007 | Nordstrom et al. | 600/323 |
| 2008/0045846 | A1* | 2/2008 | Friedman et al. | 600/490 |
| 2008/0243009 | A1 | 10/2008 | Hersh et al. | |
| 2008/0249382 | A1* | 10/2008 | Oh et al. | 600/324 |
| 2008/0262362 | A1 | 10/2008 | Kolluri et al. | |

* cited by examiner

NIBP TARGET INFLATION PRESSURE AUTOMATION USING DERIVED SPO$_2$ SIGNALS

FIELD OF THE INVENTION

The present disclosure generally relates to a method of operating an automated blood pressure measuring apparatus. More specifically, the present disclosure relates to a method of operating an automated, non-invasive blood pressure (NIBP) monitor that utilizes a separate pulse monitor to enhance the performance of the NIBP monitor.

BACKGROUND

Automated blood pressure monitoring has rapidly become an accepted and, in many cases, essential aspect of human healthcare. Such monitors are now a conventional part of the patient environment in emergency rooms, intensive and critical care units, and in the operating theater.

The oscillometric method of measuring blood pressure involves applying an inflatable cuff around an extremity of a patient's body, such as a patient's upper arm. The cuff is inflated to a pressure above the patient's systolic pressure and then the cuff pressure is reduced either continuously or incrementally in a series of small steps. A pressure sensor measures the cuff pressure, including the cuff pressure fluctuations resulting from the heart pumping activity that then causes pressure or volume oscillations in the artery under the cuff. The data from the pressure sensor is used to compute the patient's systolic pressure, mean arterial pressure (MAP) and diastolic pressure.

An example of the oscillometric method of measuring blood pressure is shown and described in U.S. Pat. Nos. 4,360,029; 4,394,034; and 4,638,810, which are commonly assigned with the present disclosure.

During the use of a conventional NIBP monitoring system, the blood pressure cuff is placed around the arm of a patient and is inflated to a pressure that fully occludes the brachial artery to prevent blood flow. The cuff is then progressively deflated and a pressure transducer detects pressure pulses as blood begins to flow past the pressure cuff. As can be understood, the selection of the initial inflation pressure determines the amount of time and deflation required before the NIBP system begins to detect cuff oscillations and blood flow. If the initial inflation pressure is selected well above the systolic blood pressure for the patient, the NIBP system over inflates the blood pressure cuff, resulting in patient discomfort and extended measurement time. Alternatively, if the initial inflation pressure is selected below the systolic blood pressure for the patient, the blood pressure cuff must re-inflate to obtain an accurate reading. Currently available monitoring systems have a target inflation pressure setting that is controlled by users to establish the initial inflation pressure. Once the monitoring system has obtained blood pressure readings for a patient, the monitoring system may use the previously determined systolic pressure value to adapt the initial inflation pressure to an individual patient. However, during the first operation of the monitoring system with a patient, the system must rely upon the selected initial inflation pressure. Therefore, it is desirable to provide a system that inflates the blood pressure cuff only slightly above the systolic pressure during the initial operation to enhance the performance of the NIBP monitoring system.

SUMMARY OF THE INVENTION

The following describes a method and system for monitoring the blood pressure in a patient that utilizes the output of a pulse monitor, such as the SpO$_2$ plethysmograph waveform from an SpO$_2$ monitor, to improve the performance of a non-invasive blood pressure (NIBP) monitor. The NIBP monitor includes a blood pressure cuff that is placed upon the limb of a patient, such as the arm or leg. The blood pressure cuff is selectively inflated and deflated by a central processor, which controls the availability of pressurized air to the cuff and the position of valves that release air from the cuff. During the deflation of the blood pressure cuff from an initial inflation pressure, oscillation pulses are detected and the central processor calculates a pulse amplitude for each oscillation pulse, such that the pulse amplitudes are utilized to calculate the blood pressure of a patient.

The combined system further includes a pulse monitor having a pulse sensor that delivers a continuous waveform, including a series of spaced pulses each representing a beat of the patient's heart, to the central processor of the NIBP monitor. In one embodiment, the pulse monitor is a pulse oximeter monitor having a finger probe sensor positioned on the finger of the patient. The finger probe sensor must be placed upon the finger of the patient on the same arm of the patient that includes the blood pressure cuff of the NIBP monitor. Alternatively, the sensor could be placed on a toe of the patient in an embodiment in which the blood pressure cuff is positioned around the leg of the patient. In such an embodiment, the sensor of the pulse monitor must still be on the same leg as the blood pressure cuff while operating within the scope of the present disclosure. The pulse oximeter monitor delivers a plethysmographic waveform to the central processor of the NIBP monitor that includes a series of spaced pulse signals each corresponding to a heartbeat of the patient.

During operation of the NIBP monitor, the central processor inflates the blood pressure cuff as quickly as possible to a pre-determined target inflation pressure. During the initial inflation of the blood pressure cuff, the central processor monitors and processes the waveform received from the pulse monitor. Since the sensor of the pulse monitor is positioned on the same arm or leg as the blood pressure cuff, as the blood pressure cuff approaches the systolic blood pressure for the patient, the waveform from the pressure sensor of the pulse monitor changes due to the lack of blood flow past the blood pressure cuff.

As the central processor receives the waveform including the series of spaced pulses from the pulse monitor, the central processor calculates a second derivative of the waveform, which corresponds to the acceleration of the waveform. During normal operation, the derived acceleration waveform includes peaks corresponding to the spaced pulses due to the patient heartbeats. As the blood pressure cuff is inflated to occlude the brachial artery of the patient, the second derivative of the pulse signals decreases. Specifically, the pulsatile component of the acceleration waveform begins to flatten out due to the blood pressure cuff occluding the artery proximal to the pulse sensor. The central processor monitors the pulses in the acceleration waveform and terminates the inflation of the blood pressure cuff when the pulses of the acceleration waveform remain below the threshold value for a predetermined period of time. The pressure at which the blood pressure cuff inflation is terminated is the initial inflation pressure for the algorithm used to operate the NIBP monitor. Since the initial inflation pressure is based upon an acceleration waveform derived from the pulses of the plethysmographic waveform, the initial inflation pressure may be above the predicted target inflation pressure or below the predicted target inflation pressure, depending upon the individual patient. Thus, the optimal initial inflation pressure is based upon measurements taken during the inflation of the blood pressure cuff, rather than estimates calculated before beginning the blood pressure monitoring process.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
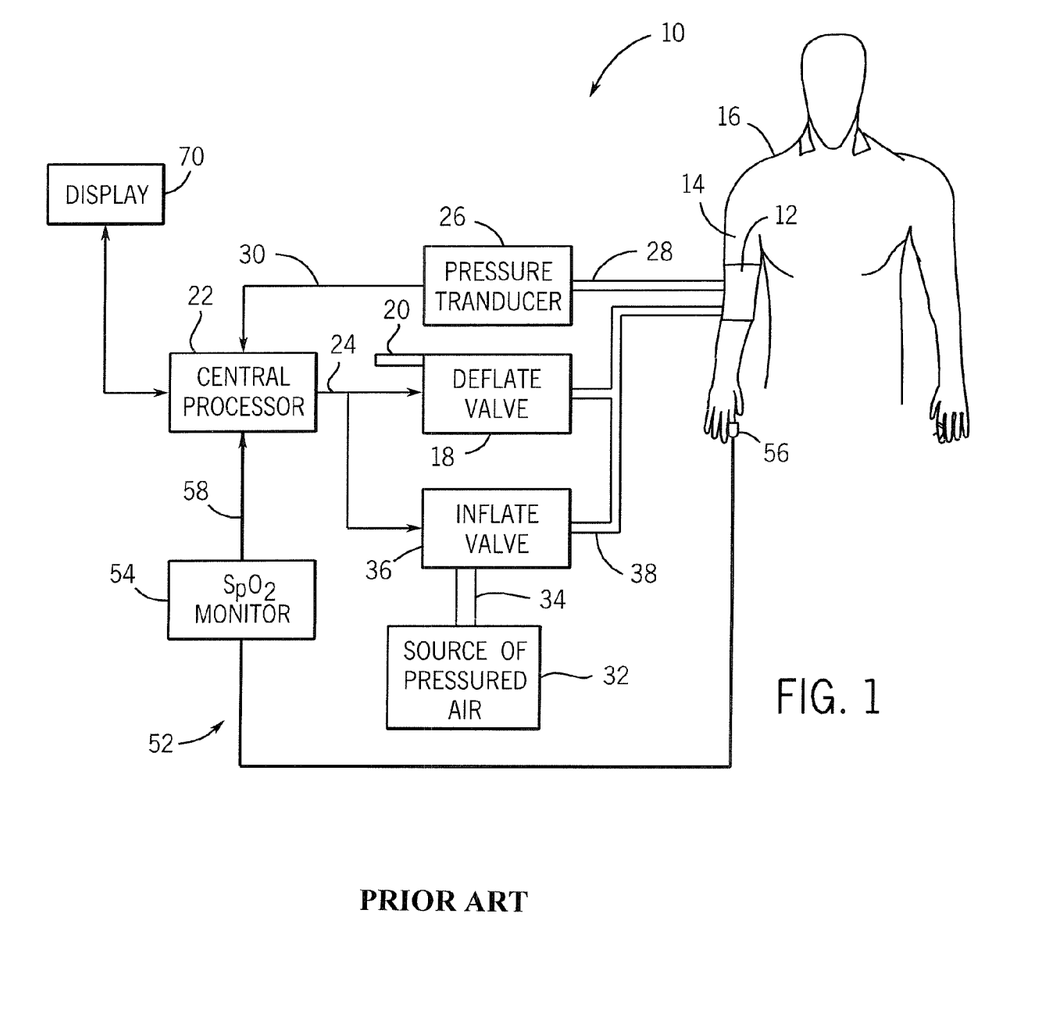
FIG. 1 is a block diagram of a system for monitoring blood pressure in a patient using an NIBP monitor and a pulse monitor.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A pressure transducer 26 is coupled by duct 28 to the blood pressure cuff 12 for sensing the pressure within the cuff 12. In accordance with conventional oscillometric techniques, the pressure transducer 26 is used to sense pressure oscillations in the cuff 12 that are generated by pressure changes in the brachial artery under the cuff. The electrical oscillation pulses from the pressure transducer 26 are obtained by the central processor 22, using an analog-to digital converter, through connection line 30.

A source of pressurized air 32, such as an air compressor or compressed gas cylinder, is connected by duct 34. In an embodiment incorporating an air compressor, the air compressor is coupled directly to the duct 38. However, if the source of pressurized air is supplied by a compressed gas cylinder, an inflate valve 36 is positioned between the source 32 and the duct 38. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the oscillation signals from first pressure transducer 26 by the central processor 22 to produce blood pressure data, and optionally to reject artifact data, can be conducted in accordance with commonly available prior art teachings. In any event, it is desirable to use any of the known techniques to determine the quality of the oscillation complexes received at each cuff pressure so that the blood pressure determination is made using the physiological relevant cuff pressure oscillations from each heartbeat and not artifacts.

Figure 2:
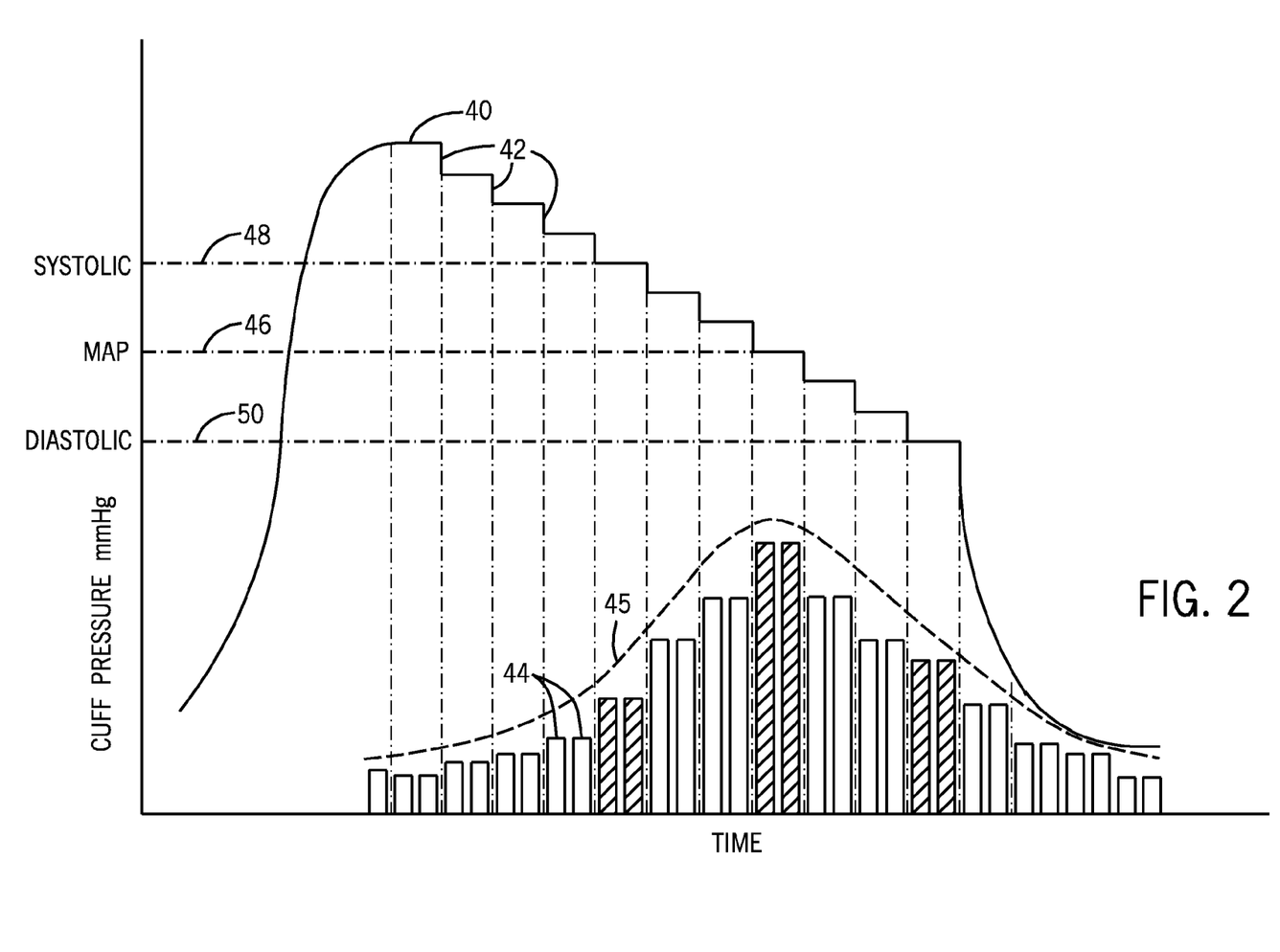
FIG. 2 is a graph depicting one method of operating an NIBP monitor by obtaining two oscillation pulse amplitudes at each of a series of pressure steps.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a target inflation pressure that fully occludes the brachial artery, i.e., prevents blood from flowing through the brachial artery at any time in the heart cycle. In FIG. 2, the target inflation pressure is illustrated by reference number 40.

After the blood pressure cuff has been inflated to the target inflation pressure 40, the deflate valve is actuated by the central processor to deflate the cuff in a series of pressure steps 42. Although various values for each pressure step 42 can be utilized, in an exemplary example, each pressure step 42 is typically about 8 mmHg per step. Alternatively, the blood pressure cuff 12 can be continuously deflated from the initial inflation pressure without the use of the discrete steps 42.

After each pressure step 42, the NIBP monitoring system detects and records the amplitude 44 of two cuff oscillation pulses for the current cuff pressure level. The pressure transducer measures the internal cuff pressure and provides an analog signal characterizing the blood pressure oscillatory complexes. The peak values of the complex signals are determined within the central processor.

As the cuff pressure decreases from the initial inflation pressure, the NIBP monitoring system detects the cuff pressure oscillations 44 and records the pressure oscillation amplitudes for the current cuff pressure. The central processor within the NIBP monitoring system can then calculate the MAP 46, systolic pressure 48 and diastolic pressure 50.

As the measurement cycles progress, the peak amplitude of the oscillation pulses generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by the central processor to calculate the mean arterial pressure (MAP) 46, the systolic pressure 48 and the diastolic pressure 50 in a known manner. The calculated blood pressure measurements are viewable on the display 70 shown in FIG. 1.

Referring back to FIG. 1, the system of the present invention further includes a pulse monitor 52 for detecting pulse signals from the patient indicative of the patient's heartbeat. In the embodiment of the invention illustrated in FIG. 1, the pulse monitor 52 is a pulse oximeter monitoring system 54 having a sensor that detects a plethysmographic signal from the patient, such as a finger probe 56 positioned on the patient 16 to determine the $SPO_2$ level of the patient 16.

Although the system in FIG. 1 illustrates the blood pressure cuff 12 positioned on the arm 14 of the patient and the finger probe 56 positioned distal from the pressure cuff 12, it should be understood that in an alternate embodiment, the pulse oximeter monitoring system 54 could be positioned at any location associated with the same arterial branch as the cuff and distal to the blood pressure cuff 12.

The pulse oximeter monitoring system 54 generates an $SpO_2$ plethysmographic signal that is provided to the central processor 22 of the NIBP monitoring system 10 through a communication line 58. In addition to providing the $SpO_2$ level for the patient, the pulse oximeter monitor 54 provides a plethysmographic waveform 60 (FIG. 3) that includes a series of pulses 62 that each result from a beat of the patient's heart. Since the finger probe 56 is attached to the patient 16 at all times, the pulse oximeter monitor 54 continuously monitors the patient and generates the continuous plethysmographic waveform 60 having the series of time-spaced pulses 62.

Although a pulse oximeter monitor 54 is shown and described in the embodiment of FIG. 1, it should be understood that other types of pulse monitoring systems and sensors can be utilized while operating within the scope of the present disclosure. As an example, an impedance plethysmograph monitor can be placed on the finger or wrist, a piezoelectric sensor could be utilized on the wrist of the patient or any other means of sensing the blood volume pulse within the patient and distal to the blood pressure cuff can be utilized while operating within the scope of the present disclosure.

Figure 3:
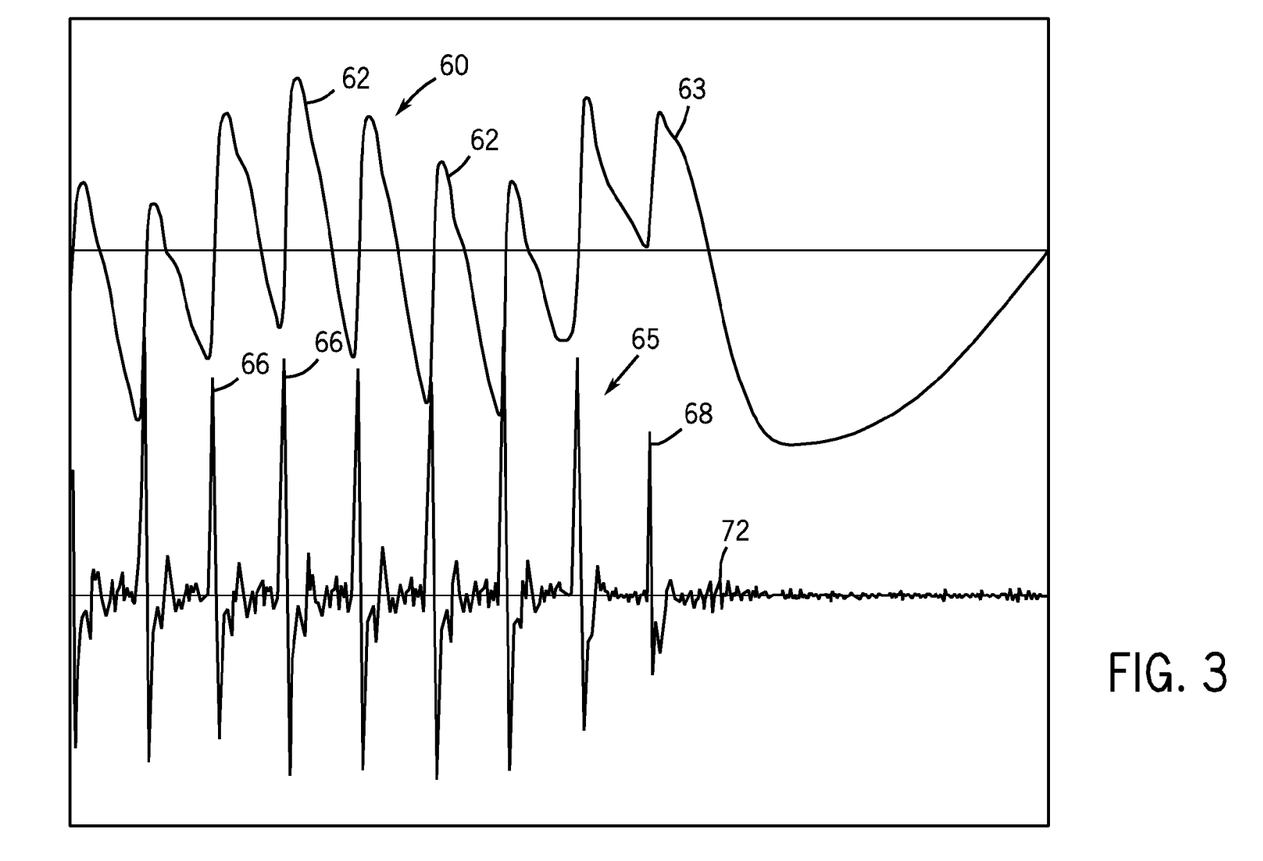
FIG. 3 illustrates the plethysmographic waveform including a series of spaced pulses and the second derivative of the waveform, referred to as the acceleration of the plethysmographic waveform.

Referring back to FIG. 3, the plethysmograph waveform 60 includes a series of pulses 62 that each represent a beat of the patient's heart. In the graph of FIG. 3, the waveform 60 is illustrated as the blood pressure cuff on the patient is inflated to ultimately occlude the brachial artery. The occlusion of the brachial artery occurs following the final pulse 63 of FIG. 3. After the final pulse 63, the waveform 60 falls dramatically and no additional pulses 62 are detected. No additional pulses are detected since the brachial artery has been fully occluded and no additional blood flow reaches the finger probe sensor of the pulse monitor.

FIG. 3 further illustrates an acceleration waveform 65 which is a second derivative of the plethysmograph waveform 60. The acceleration waveform 65 includes a series of acceleration peaks 66 that each correspond to the rapidly rising portion of the plethysmograph waveform 60 that occurs at the beginning of each of the pulses 62. The individual peaks 66 of the acceleration waveform 65 occur at the same frequency as the patient's heart rate, as clearly illustrated in FIG. 3.

When the blood pressure cuff begins to occlude the brachial artery, the pulses 62 begin to disappear following the final pulse 63. Since the pulses 62 disappear after the complete occlusion of the brachial artery, the acceleration waveform flattens out after the final acceleration peak 68. The flattened portion of the acceleration signal 65 is shown by reference numeral 72. The flattened portion 72 indicates that the brachial artery has been fully occluded by the blood pressure cuff, indicating that the NIBP monitoring system has inflated the blood pressure cuff above the systolic pressure for the patient and that no further inflation is needed.

The acceleration waveform 65 shown in FIG. 3 is a second derivative of the plethysmograph waveform 60 and is not subject to the low frequency variation present in the plethysmograph waveform 60. By utilizing the acceleration waveform 65 rather than the plethysmograph waveform 60, a more reliable determination of when the brachial artery is fully occluded can be determined. The acceleration waveform 65 identifies the beginning of the heart pulse with greater accuracy than can be made using the plethysmograph waveform 60. Additionally, the detection of the pulse occurs sooner in time in the acceleration waveform 65 relative to the cuff oscillation pulses, thereby making the process of identification of the proper initial target pressure occur sooner and in a more deterministic manner.

In the embodiment of the disclosure shown in FIG. 1, the central processor 22 of the NIBP monitoring system 10 receives the plethysmograph waveform from the pulse oximeter monitoring system 54 and calculates the second derivative of the plethysmograph waveform to create the acceleration waveform 65. However, it is contemplated that the pulse oximeter monitoring system 54 could also perform the second derivative calculation and provide the acceleration waveform directly to the central processor 22.

Prior to beginning operation of the NIBP monitoring system to determine the patient blood pressure, the pulse sensor within the finger probe detects a series of individual pulses 62 that each result from a beat of the patient's heart. The continuous plethysmograph waveform 60 from the finger probe is obtained by the $SpO_2$ monitor 54 and relayed to the central processor 22 of the NIBP monitoring system 10, as illustrated in FIG. 1. As discussed above, the central processor 22 of the NIBP monitoring system 10 can then calculate the acceleration waveform 65 in the manner previously described.

Figure 4:
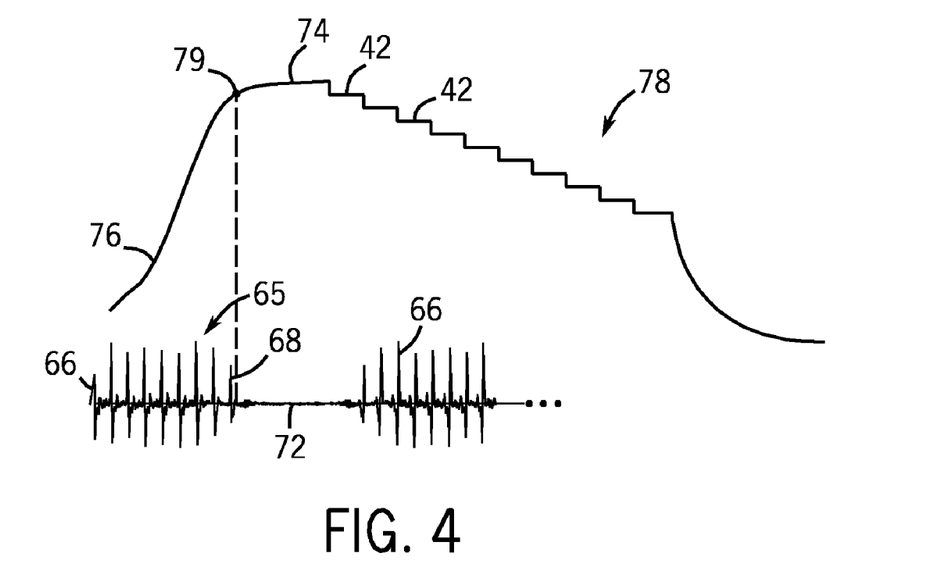
FIG. 4 illustrates the acceleration of the plethysmographic waveform as the blood pressure cuff of the NIBP monitor is inflated to a target inflation pressure.

When the NIBP monitoring system begins operation, the blood pressure cuff 12 positioned on the arm of the patient is rapidly inflated from a very low pressure to a target inflation pressure 74, as indicated by the steeply sloped portion 76 of the cuff pressure profile 78 of FIG. 4. Since the blood pressure cuff and the finger probe are positioned on the same arm or leg of the patient, as the cuff pressure increases near and above the systolic pressure for the patient, as shown by pressure level 79, the acceleration peaks 66 of the acceleration waveform 65 disappear following the final peak 68. Once the cuff pressure exceeds the systolic pressure for the patient, the blood flow through the brachial artery past the blood pressure cuff is terminated such that the acceleration peaks 66 are no longer present in the acceleration waveform 65, as illustrated by the flat portion 72 of the acceleration waveform 65.

Once the cuff pressure 78 decreases below the systolic blood pressure 79 through the series of pressure steps 42 to allow blood to flow past the blood pressure cuff, the flat portion 72 terminates and acceleration peaks 66 return until the complete blood flow returns and the full size acceleration peaks 66 are again present within the acceleration waveform 65. As can be understood in FIG. 4, the pressure at which the acceleration peaks 66 disappear is an indication that the blood pressure cuff has been inflated to a pressure sufficient to restrict the flow of blood past the blood pressure cuff, as detected by the sensor within the finger probe 56. Thus, once the acceleration peaks 66 have been eliminated, inflation of the blood pressure cuff can be terminated, since the cuff pressure is above the systolic pressure for the patient. As can be understood in FIG. 1, the finger probe 56 must be placed at the same arm or leg of the patient as the blood pressure cuff 12 to identify the initial inflation pressure for the patient upon inflation of the blood pressure cuff 12.

Figure 5:
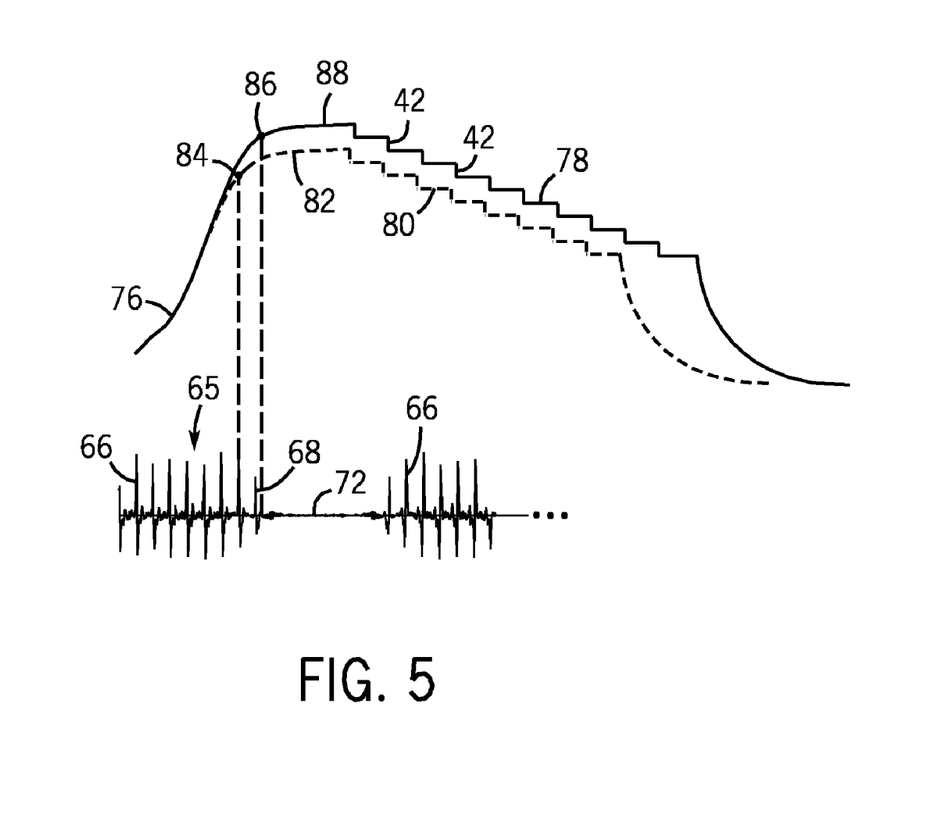
FIG. 5 is a graphical illustration of the acceleration of the plethysmographic waveform and the adjusted initial inflation pressure of the blood pressure cuff.

Referring now to FIG. 5, there shown is a first operational example utilizing the method and system of the present disclosure. The dashed line shown in FIG. 5 represents an estimated cuff inflation curve 80 predicted by the central processor of the NIBP monitoring system. The predicted curve 80 included a target inflation pressure 82 that is predetermined by the central processor based upon a typical patient before beginning the blood pressure determination procedure. The selection of the target inflation pressure 82 is oftentimes difficult for the NIBP monitoring system during the first iteration of determining the patient's blood pressure since the NIBP monitoring system does not have any previous blood pressure measurement values for the specific patient upon which to base an estimation for the target inflation pressure 82. Further, since the NIBP monitoring system may be moved from patient to patient within a hospital or critical care environment, the selection of the target inflation pressure is typically a standard value and is not patient-dependent.

FIG. 5 illustrates a situation in which the predicted target inflation pressure 82 is too low for the individual patient. As illustrated, as the cuff pressure 78 increases during the sloped initial inflation portion 76, the acceleration peaks 66 of the acceleration waveform 65 remain generally constant, even as the cuff pressure 78 reaches the predicted inflation termination point 84, at which time the cuff inflation would have ceased to inflate the cuff to the target inflation pressure 82. Since the acceleration peaks 66 are still present when the cuff pressure reaches the target inflation pressure 82, the cuff pressure has not yet reached the systolic pressure for the patient. Since the systolic pressure has not been reached by the target inflation pressure 82, the central processor operating in accordance with the present disclosure continues to inflate the blood pressure cuff until the central processor detects the disappearance of acceleration peaks following the last peak 68.

Once the acceleration peaks 66 are no longer present, the inflation of the blood pressure cuff is terminated at point 86 and the cuff reaches an initial inflation pressure 88. In the example illustrated in FIG. 5, the initial inflation pressure 88 is well above the predicted target inflation pressure 82. If the NIBP monitoring system were operated utilizing only the target inflation pressure 82, the inflation pressure of the blood pressure cuff would have been insufficient and the blood pressure cuff would have needed to be re-inflated to a higher pressure target pressure to obtain an accurate blood pressure reading. However, by utilizing the plethysmograph acceleration waveform 65, the NIBP monitoring system automatically increased the initial inflation pressure of the blood pressure cuff until the central processor detected the disappearance of the acceleration peaks. After reaching the initial inflation pressure 88, the cuff pressure is decreased in the series of pressure steps 42 and the blood pressure is determined utilizing oscillation pulse amplitudes in the known manner described previously.

Figure 6:
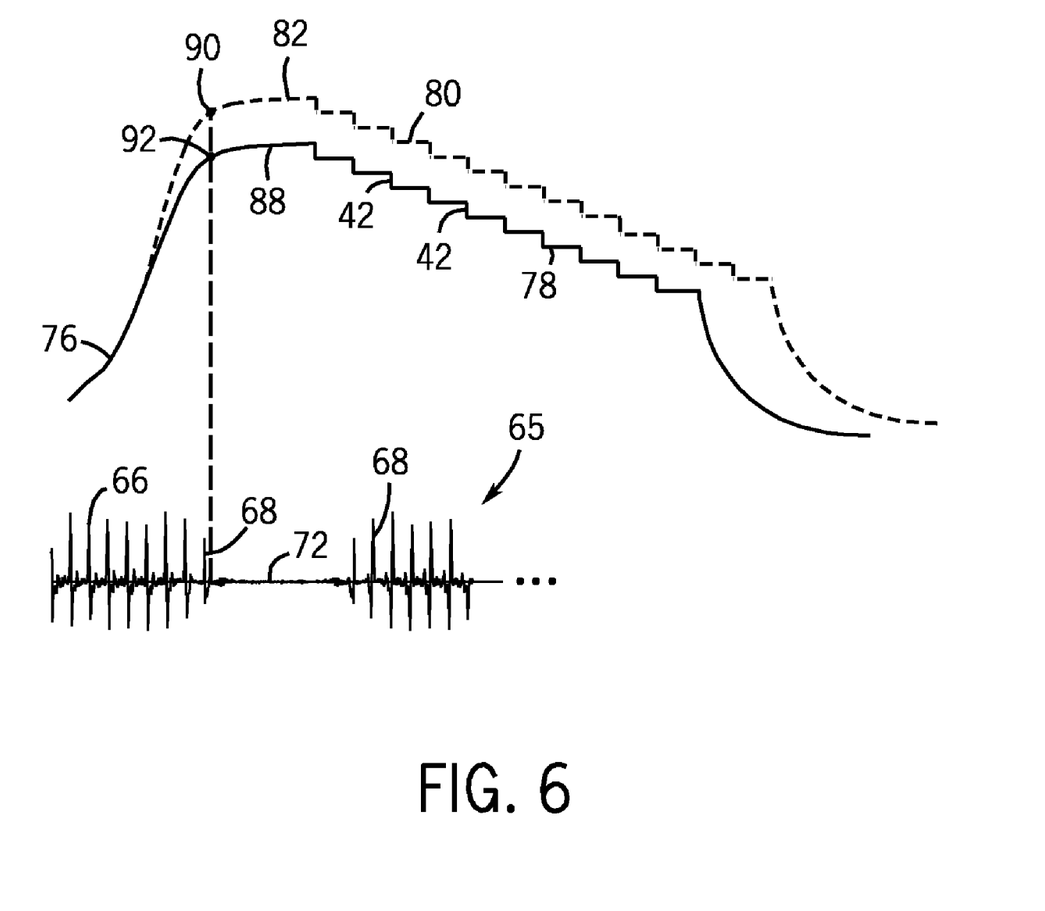
FIG. 6 is a graphical illustration of the acceleration of the plethysmographic waveform and the adjusted initial inflation pressure of the blood pressure cuff.

Referring now to FIG. 6, there shown is an example of the operation of the combined NIBP monitoring system when the predicted target inflation pressure 82 is too high for the individual patient. In the embodiment illustrated in FIG. 6, the predicted cuff inflation profile 80 is again shown in dashed lines. Like the embodiment illustrated in FIG. 5, the central processor of the NIBP monitoring system initially predicts the target inflation pressure 82. However, as the cuff pressure 78 increases during the sloped portion 76 and reaches point 90, the acceleration peaks 66 disappear at a cuff pressure well below the target inflation pressure 82, as shown following the last acceleration peak 68. When the central processor 22 detects the disappearance of the peaks following the last peak 68 before the cuff pressure reaches the predicted target inflation pressure 82, the central processor terminates the inflation of the blood pressure cuff at point 92 to define the initial inflation pressure 88.

In the example illustrated in FIG. 6, the initial inflation pressure 88 is well below the target inflation pressure 82. If the NIBP monitoring system utilized the predicted target inflation pressure 82, the blood pressure cuff would be over-inflated, leading to patient discomfort and increased time required to obtain a blood pressure measurement. As discussed previously, once the blood pressure cuff reaches the initial inflation pressure 88, the cuff pressure is reduced in the series of pressure steps 42 and the oscillation pulse amplitudes are utilized to calculate a blood pressure estimate for the patient in accordance with known methods.

As discussed above in the two examples shown in FIGS. 5 and 6, the central processor 22 of the NIBP monitoring system 10 terminates the inflation of the blood pressure cuff upon detection of the disappearance of the acceleration peaks 68. The determination of when the acceleration peaks have disappeared to indicate that the blood pressure cuff has been properly inflated can be based upon various properties of the individual acceleration peaks 66. As an example, the inflation of the blood pressure cuff could be terminated when the acceleration peaks fall below either a predetermined threshold value or fall a selected percentage below a standard acceleration peak. This determination can be made within the central processor 22 of the NIBP monitoring system 10 shown in FIG. 1.

Alternatively, the comparison could also be based upon a rate of change between the current acceleration peak and the previous acceleration peak. When the rate of change exceeds a selected value, the central processor 22 determines that the inflation of the blood pressure cuff is sufficient and should be terminated. As indicated previously, the use of the acceleration waveform 65 as compared to the plethysmograph waveform 60 shown in FIG. 3 allows the NIBP monitoring system 10 to more accurately monitor pulse timing and position and to eliminate low frequency noise from the finger probe in the determination of when to terminate inflation of the blood pressure cuff.

Figure 7:
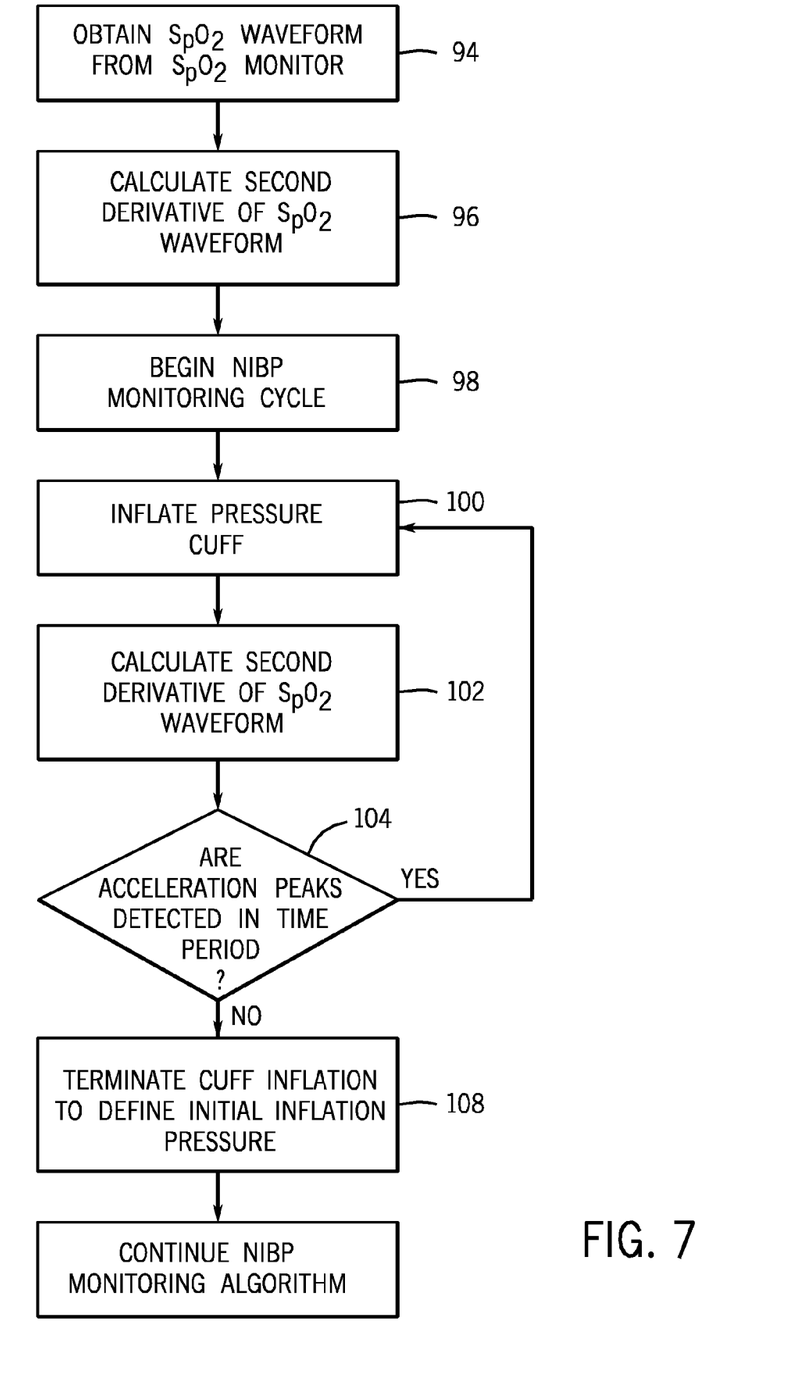
FIG. 7 is a flowchart illustrating the operational sequence utilized by the system and method of the present disclosure to determine the blood pressure of a patient using an NIBP monitor and a pulse oximeter monitor.

FIG. 7 illustrates a flowchart of the operational sequence of the NIBP monitoring system in accordance with the one embodiment of the present disclosure. As illustrated in FIG. 7, the NIBP monitoring system continuously receives a plethysmographic waveform from the pulse monitor, as illustrated in step 94. The central processor of the NIBP monitoring system receives the continuous waveform and calculates the second derivative of the plethysmograph waveform, as indicated in step 96. As described previously, the second derivative of the plethysmograph waveform 60 shown in FIG. 3 includes a series of acceleration peaks 66.

After the acceleration waveform 65 has been calculated, the central processor begins the normal NIBP monitoring cycle in step 98 by inflating the blood pressure cuff in step 100. As shown in FIG. 4, the blood pressure cuff is initially inflated along the steeply sloped portion 76 from a nearly zero pressure level to a target inflation pressure 74. As the blood pressure cuff is inflated, the central processor receives the continuous plethysmographic waveform from the $SpO_2$ monitor. As the blood pressure cuff is inflated, the central processor receives the plethysmograph waveform 60 and calculates the second derivative (acceleration waveform) in step 102.

After calculating the second derivative of the plethysmograph waveform, the central processor determines in step 104 whether the acceleration waveform 65 includes the acceleration peaks 66. Specifically, the central processor determines whether an acceleration peak 66 is detected within a predetermined time period. As one example, the time period could be the heart rate of the patient. If no acceleration peak is detected, then the system concludes that the blood pressure cuff has been fully inflated above the systolic pressure and that no further inflation is required. If no acceleration peak is detected, the system proceeds to step 108 and terminates the cuff inflation to define the initial inflation pressure.

As illustrated in FIGS. 5 and 6, when the central processor determines that the inflation of the blood pressure cuff is no longer required, the initial inflation pressure 88 may be above or below the target inflation pressure 82 selected by the central processor. The use of the acceleration waveform 65 to set the initial inflation pressure 88 allows the NIBP monitoring system to set the initial inflation pressure based upon information gathered during the inflation of the blood pressure cuff, rather than an estimate calculated prior to the initiation of the NIBP monitoring cycle. Once the cuff pressure has been set at the initial inflation pressure, the central processor operates in accordance with a known NIBP monitoring algorithm to detect oscillation pulse amplitudes and calculate the blood pressure of the patient.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring blood pressure in a patient, the method comprising the steps of:
    providing a pulse monitor having a sensor operable to detect pulse signals due to the patient's heartbeat;
    positioning a blood pressure cuff on the patient;
    positioning the sensor on the patient distal to the blood pressure cuff to detect pulse signals from the patient;
    inflating the blood pressure cuff;
    calculating, using a central processor, a second derivative of the pulse signals during inflation of the blood pressure cuff, the second derivative including a series of acceleration pulse peaks;
    reducing low frequency variations in the pulse signals based on the calculated second derivative of the pulse signals; and
    terminating the inflation of the blood pressure cuff based upon the acceleration pulse peaks in the calculated second derivative of the pulse signals; and
    defining an initial target pressure after terminating the inflation of the blood pressure cuff.

2. The method of claim 1 wherein the pulse monitor sensor is positioned on a finger of the patient.

3. The method of claim 2 wherein the pulse monitor is an SpO$_2$ monitor and the sensor is an SpO$_2$ sensor positioned on the finger of the patient.

4. The method of claim 1 wherein the inflation of the blood pressure cuff is terminated upon the absence of the acceleration pulse peaks.

5. The method of claim 1 wherein the inflation of the blood pressure cuff is terminated based upon the attenuation of the acceleration pulse peaks during the inflation of the blood pressure cuff.

6. The method of claim 1 wherein the pulse monitor is an SpO$_2$ monitor and the sensor is an SpO$_2$ sensor positioned on a finger of the patient.

7. The method of claim 1 wherein the blood pressure cuff and the sensor of the pulse monitor are positioned along the same arterial branch of the patient.

8. A method of operating a non-invasive blood pressure (NIBP) monitor having a central processor, a blood pressure cuff positionable on an arm of the patient and a pressure transducer operable to detect oscillation pulses beneath the blood pressure cuff, the method comprising the steps of:
    providing a pulse monitor having a sensor positioned to detect a pulse waveform having a plurality of pulses from the patient representative of the patient's heartbeat;
    positioning a blood pressure cuff on an arm of the patient;
    positioning the sensor of the pulse monitor on the same arm of the patient and anatomically distal to the blood pressure cuff;
    inflating the blood pressure cuff to begin to occlude an artery in the arm of the patient;
    calculating, using the central processor, a second derivative of the pulse waveform during inflation of the blood pressure cuff, the second derivative including a series of acceleration pulse peaks;
    reducing low frequency variations in the pulse waveform based on the calculated second derivative of the pulse waveform; and
    terminating the inflation of the blood pressure cuff based upon the acceleration pulse peaks in the calculated second derivative of the pulse waveform; and
    defining an initial target pressure after terminating the inflation of the blood pressure cuff;
    decreasing the pressure in the blood pressure cuff from the initial inflation pressure while monitoring for oscillation pulses from the pressure transducer; and
    calculating the systolic pressure, mean arterial pressure and diastolic pressure for the patient based upon the cuff oscillation pulses detected during the deflation of the blood pressure cuff.

9. The method of claim 8 wherein the central processor of the NIBP monitor is in communication with the pulse monitor such that the central processor calculates the second derivative based on the pulse waveform from the pulse monitor.

10. The method of claim 8 wherein the pulse monitor is an SpO$_2$ monitor and the sensor is an SpO$_2$ finger probe.

11. The method of claim 8 wherein the central processor defines a target inflation pressure for the patient, the method further comprising the steps of:
    inflating the blood pressure cuff to the target inflation pressure;
    reducing the target inflation pressure upon the absence of the acceleration peaks prior to inflation of the blood pressure cuff to the target inflation pressure; and
    increasing the target inflation pressure upon the presence of the acceleration peaks when the blood pressure cuff is inflated to the target inflation pressure.

12. The method of claim 8 wherein the sensor of the pulse monitor and the blood pressure cuff are positioned along the same arterial branch of the patient.

13. The method of claim 8 wherein the inflation of the blood pressure cuff is terminated upon the absence of the acceleration pulse peaks.

14. The method of claim 8 wherein the inflation of the blood pressure cuff is terminated based upon the attenuation of the acceleration pulse peaks.

15. A system for determining the blood pressure of a patient, comprising:
    a non-invasive blood pressure (NIBP) monitor including a central processor and a display;
    a blood pressure cuff positionable on the patient, the blood pressure cuff being selectively inflatable and deflatable by the NIBP monitor;
    a pressure transducer operable to measure the pressure within the blood pressure cuff and coupled to the central processor, the pressure transducer being operable to detect oscillation pulses from the patient; and a pulse monitoring system having a sensor positionable on the patient to detect pulse signals from the patient due to the patient's heartbeat, wherein the central processor calculates a second derivative of the pulse signals;

reduces low frequency variation in the pulse signals; and controls the inflation of the blood pressure cuff based upon the calculated second derivative.

16. The system of claim 15 wherein the pulse monitoring system is an $SpO_2$ monitor having a finger probe.

17. The system of claim 15 wherein the central processor controls the inflation of the blood pressure cuff based upon the presence and absence of acceleration pulse peaks in the calculated second derivative.

* * * * *